United States Patent
Denys et al.

(10) Patent No.: US 11,844,885 B2
(45) Date of Patent: Dec. 19, 2023

(54) PHOTOCATALYTIC REACTOR FOR VENTILATION SYSTEMS

(71) Applicants: UNIVERSITEIT ANTWERPEN, Antwerp (BE); VENTO NV, Oudenaarde (BE)

(72) Inventors: Siegfried Denys, Oudenaarde (BE); Jeroen Van Walsem, Waasmunster (BE); Silvia Lenaerts, Berchem (BE); Bart Modde, Brakel (BE); Jelle Roegiers, Assenede (BE)

(73) Assignees: UNIVERSITEIT ANTWERPEN, Antwerp (BE); VENTO NV, Oudenaarde (BE)

( * ) Notice: Subject to any disclaimer, the term of this patent is extended or adjusted under 35 U.S.C. 154(b) by 0 days.

(21) Appl. No.: 16/626,087

(22) PCT Filed: Jun. 28, 2018

(86) PCT No.: PCT/EP2018/067348
§ 371 (c)(1),
(2) Date: Dec. 23, 2019

(87) PCT Pub. No.: WO2019/002430
PCT Pub. Date: Jan. 3, 2019

(65) Prior Publication Data
US 2020/0206381 A1    Jul. 2, 2020

(30) Foreign Application Priority Data
Jun. 28, 2017    (EP) .................................... 17178547

(51) Int. Cl.
*A61L 9/20*    (2006.01)
*B01J 35/00*    (2006.01)
*F24F 8/22*    (2021.01)

(52) U.S. Cl.
CPC ............. *A61L 9/205* (2013.01); *B01J 35/004* (2013.01); *F24F 8/22* (2021.01);
(Continued)

(58) Field of Classification Search
CPC ............... A61L 9/205; A61L 2209/111; A61L 2209/12; A61L 2209/16; B01J 35/004;
(Continued)

(56) References Cited

U.S. PATENT DOCUMENTS 5,778,664 A * 7/1998 Janata .................. B01D 53/007
60/274
5,875,384 A    2/1999 Peill et al.
(Continued)

FOREIGN PATENT DOCUMENTS

FR    2920670 A1    3/2009
JP    2001104460 A    4/2001

OTHER PUBLICATIONS

European Search Report from EP Application No. 17178547.0, dated Jan. 3, 2018.
(Continued)

*Primary Examiner* — Xiuyu Tai
(74) *Attorney, Agent, or Firm* — WORKMAN NYDEGGER

(57) ABSTRACT

A photocatalytic reactor for use in a heating, ventilation and/or air conditioning system, and comprises a longitudinal housing having a wall and allowing air or gas to pass through along the longitudinal direction of the longitudinal housing. A plurality of tubes are positioned in the longitudinal housing and arranged such that some outer tubes are positioned closer to the housing wall than some inner tubes. The tubes have their longitudinal axis parallel with the longitudinal axis of the longitudinal housing allowing the air or gas to pass along and through the tubes and the tubes
(Continued)

comprise photocatalytic material in or on their tube walls. The system comprises an irradiation system for irradiating the photocatalytic material for inducing catalytic action. The irradiation system and plurality of tubes are configured so that upon irradiating by the irradiation system photocatalytic material of the outer tubes and inner tubes is irradiated.

20 Claims, 15 Drawing Sheets

(52) U.S. Cl.
CPC ...... *A61L 2209/111* (2013.01); *A61L 2209/12* (2013.01); *A61L 2209/16* (2013.01)

(58) Field of Classification Search
CPC ........ B01J 2219/0809; B01J 2219/0892; B01J 19/127; B01J 19/0053; B01J 19/2405; B01J 19/2425; B01J 2219/0877; B01J 2219/0002; F24F 3/16; F24F 8/22; C02F 1/30; C02F 1/325; C02F 2305/023; C02F 2201/3228; C02F 2305/10; C02F 2201/328; C02F 2201/3224; C02F 1/725; B01H 5/0688; B01F 13/0059; B01F 5/0682; Y02W 10/37

See application file for complete search history.

(56) References Cited

U.S. PATENT DOCUMENTS

| | | | |
|---|---|---|---|
| 6,135,838 | A | 10/2000 | Wang |
| 6,558,639 | B1 * | 5/2003 | Watanabe ............ B01J 19/123 |
| | | | 422/186.3 |
| 2005/0129853 | A1 * | 6/2005 | Wang .................... C04B 41/87 |
| | | | 427/372.2 |
| 2007/0181508 | A1 | 8/2007 | Gui et al. |
| 2013/0142692 | A1 | 6/2013 | Tarifi |
| 2014/0037497 | A1 | 2/2014 | Hayman, Jr. |
| 2016/0317693 | A1 | 11/2016 | Greist |

OTHER PUBLICATIONS

International Search Report and Written Opinion from PCT Application No. PCT/EP2018/067348, dated Jan. 2, 2019.

* cited by examiner

PHOTOCATALYTIC REACTOR FOR VENTILATION SYSTEMS

FIELD OF THE INVENTION

The invention relates to the field of photocatalytic oxidation for air or gas purification. More particularly, the present invention relates to methods and systems for photocatalytic oxidation in heating, ventilation and/or air conditioning systems.

BACKGROUND OF THE INVENTION

Indoor air quality (IAQ) has become of vital importance to health globally—especially in the developed countries where people generally spend more than 80% of their time in an indoor environment e.g. at home, school, office, public buildings and gyms. Many volatile organic compounds (VOCs) have been identified indoors which are hazardous substances emitted from construction materials, indoor equipment or human indoor activities such as cooking or heating. VOCs may trigger the sick building syndrome (SBS), which covers the broad range of health problems caused by bad IAQ. Nowadays, ventilation systems D (balanced ventilation) are commonly used to maintain the indoor air quality. These systems are automatically controlled by mechanical air supply and exhaust through fans. A network of pipes throughout the building supplies fresh air in each room. The main disadvantages of these systems include the high energy consumption of the fans, heat losses and the dependency on the outdoor air quality (OAQ). To ensure a healthy IAQ, a wise strategy is to combine ventilation and air purification. Of the advanced air purification methods, photocatalytic oxidation (PCO) is a promising technique for integration into heating, ventilation and air conditioning (HVAC) systems. PCO technology exposes a catalyst, mostly titanium dioxide $TiO_2$, to ultraviolet (UVA) light to produce hydroxyl radicals and superoxide anions. These radicals are extremely reactive and are able to mineralize VOCs into $H_2O$ and $CO_2$. The advantage of using an air purification device is that the IAQ can be maintained with a minimum of ventilation, resulting in less energy consumption and even a contribution to a better OAQ. PCO is an interesting, cost-effective and efficient approach for indoor air pollution abatement but its commercialization is decelerated by the many requirements of a PCO device or reactor and the substrate for the photocatalyst. There is still a substantial gap to be filled between lab-scale investigation of suitable photocatalysts and applied PCO technology for air purification. The design of an effective photocatalytic reactor is the main issue in commercializing PCO technology. Different types of lab-scale photocatalytic devices have been extensively studied in the past, such as batch reactors, annular reactors, honeycomb monolith reactors, flat bed reactors, fluidized bed reactors, glass fiber reactors, glass beads reactors, spiral reactor and multi-tube reactors. Each of these reactor designs are based on difference performance criteria, but generally it can be stated that an efficient PCO reactor should achieve complete mineralization of VOCs, high proton utilization of the photocatalyst, low pressure drop and power consumption in a relatively compact vessel. Indeed, integration or retrofitting of a PCO device into a HVAC system requires special features to deal with the typical high flow rates. The photocatalytic substrate advantageously must allow the contaminated air to pass through with a minimal pressure drop, permit sufficient contact time between VOC and photocatalyst, have a high surface area available for coating with excellent adherence and be permeable for UV light.

SUMMARY OF THE INVENTION

It is an object of the present invention to provide photocatalytic reactors which are easily implementable in an existing or new HVAC system.

It is an advantage of embodiments of the present invention that photocatalytic reactors are obtained that provide good airflow resistance properties at typical air velocities in a ventilation system.

It is an advantage of embodiments of the present invention that the substrates for photocatalytic reaction used can be aligned with the air flow, thus minimizing the pressure drop in the ventilation system by friction losses.

It is an advantage of embodiments of the present invention that photocatalytic reactors can be provided allowing to be introduced in HVAC systems whereby use typically can be made of the fan(s) or blower(s) present in the HVAC system without the need of requiring a separate own ventilation unit for the photocatalytic reactor.

It is an advantage of embodiments of the present invention that the additional energy demand due to pressure losses in the photocatalytic reactor can be limited.

It is an advantage of embodiments of the present invention that the photocatalytic reactors provide a sufficiently open structure to limit the pressure loss while at the same time provide a sufficient large exposed surface area to allow interaction between the contaminant and the photocatalyst so that the photocatalytic reaction proceeds as completely as possible.

It is an advantage of embodiments of the present invention that the photocatalytic reactors do not introduced large pressure losses which could lead to malfunctioning of the fan or blower(s).

It is an advantage of embodiments of the present invention that photocatalytic reactors are provided that show a good photocatalyst coating adhesion properties when used in ventilation systems.

It is an advantage of embodiments of the present invention that photocatalytic reactors are provided that show good light permeability.

It is an advantage of embodiments of the present invention that photocatalytic reactors are provided that show high photocatalytic activity towards the degradation of volatile organic compounds in air.

It is an advantage of embodiments of the present invention that photocatalytic reactors are provided whereby the substrates used are made of relatively cheap materials.

The above object and optionally one or more of the advantages is obtained by methods and systems according to the present invention.

The present invention relates to a photocatalytic reactor for use in a heating, ventilation and/or air conditioning system, the photocatalytic reactor comprising
a longitudinal housing, the longitudinal housing having a wall and comprising an inlet and an outlet for allowing air or gas to pass through along the longitudinal direction of the longitudinal housing,
a plurality of tubes positioned in the longitudinal housing and arranged such that some outer tubes are positioned closer to the housing wall than some inner tubes, said plurality of tubes having their longitudinal axis parallel with the longitudinal axis of the longitudinal housing allowing said air or gas to pass along and through said tubes, said tubes furthermore comprising photocatalytic material in or on their tube walls, and an irradiation system for irradiating the photocatalytic material for inducing catalytic action, wherein the irradiation system and plurality of tubes are configured so that upon irradiating by the irradiation system photocatalytic material of said outer tubes as well as of said inner tubes is irradiated. The photocatalytic material may be a coating on the tube walls. The photocatalytic material may be embedded in the walls of the tubes. The wall of the housing may be transparent, for example when radiation sources outside the housing are used for inducing the photocatalytic effect. The irradiation system may be a UV source, e.g. a UV-A and/or UV-C irradiation source.

The tubes may be glass tubes.

The tubes may be made of sodium free glass. It is an advantage of embodiments of the present invention that tubes are used suitable for good sticking properties between the photocatalytic material and the tubes.

The photocatalytic material applied may be applied using a method of applying photocatalytic material comprising a calcination step.

The cross-section of the tubes may be any or a combination of circular, elliptical or polygonal. There even may be irregularity in the cross-sections. The tubes do not need to have a constant cross-section. Not all tubes need to have the same cross-section.

The tubes may be geometrically arranged such that the outer walls of the tubes form feedthroughs for air or gas to pass. For each feedthrough, the cross-sectional area may be between 0.5 and 1.5 of the average cross-sectional area of the tubes. It is an advantage of embodiments of the present invention that both inner sides and outer sides of the tubes can be used efficiently for photocatalytic reaction, since the pressured drop is substantially equal both in the tubes as in the feedthrough in between the claims.

The irradiation system also may comprise reflectors for guiding radiation towards the photocatalytic material.

As indicated above the walls of the housing may be transparent or at least partly transparent for activation radiation stemming from outside the housing. Alternatively, if the full irradiation system is internal of the housing, the walls of the housing may be reflective such that radiation reaching the walls is back reflected towards the tubes.

The number of tubes in the longitudinal housing may be four or more.

The tubes may be made of a material that is at least partly transparent for irradiation of said irradiation system. The tubes may be made of glass or quartz, such as for example borosilicate glass, although embodiments are not limited thereto. For example, also plastics that are UV transparent could be used, or any other type of material that is UV transparent and can be coated with the photocatalyst, prior or after coating.

Because of the transparency of the tubes, photocatalytic material on or in inner tubes also can be irradiated.

The photocatalytic material may be positioned at an inner wall of the tubes, at an outer wall of the tubes or both at an inner wall and an outer wall of the tubes.

The tubes may be stacked in a closed stacking configuration. It is an advantage of embodiments of the present invention that a large active surface may be obtained for photocatalytic reaction.

The irradiation system may comprise one or more UV sources positioned outside the longitudinal housing.

The UV source(s) may be a UV-A and/or a UV-C source.

The irradiation system may comprise at least two UV sources being positioned at opposite sides outside the housing. The irradiation sources may be elongated irradiation sources positioned substantially parallel with the longitudinal housing.

The irradiation system may comprise longitudinal irradiation sources positioned in the housing in between at least some outer tubes and at least some inner tubes.

The longitudinal irradiation sources may comprise optical fibers in between at least some outer tubes and at least some inner tubes, said optical fibers being arranged for guiding irradiation from an irradiation source couplable or in connection thereto.

The photocatalytic material may comprises titaniumdioxide. Other examples of possible photocatalytic materials are $ZnO$, $Cu_xO$, $Fe_2O_3$, $CdS$, $GaP$, $ZnS$, $WO_3$, etc.

The longitudinal housing may have a cross-section substantially corresponding with a cross-section of a conventional section of a heating, ventilation and/or conditioning system. It is an advantage of embodiments of the present invention that the photocatalytic reactor can be made such that it can easily replace an existing section of a HVAC system. Since typically also no additional fan or pumping unit is required, upgrading or maintaining a HVAC system can be done in an easy way.

The present invention furthermore relates to a photocatalytic reactor system comprising a photocatalytic reactor as described above, wherein the photocatalytic reactor system furthermore comprises one or more filters for first adsorbing VOC's and optional additional pollutants from a flow and for thereafter, when one of the filters is saturated, releasing the VOC's and the optional additional pollutants, the photocatalytic reactor system furthermore being adapted for treating the released VOC's and optional additional pollutants using the photocatalytic reactor.

The present invention also relates to a heating, ventilation and/or air conditioning system comprising a photocatalytic reactor as described above.

The transport of air or gas in the photocatalytic reactor may be solely based on a fan or pumping unit of the heating, ventilation and/or air conditioning system.

The system furthermore may comprise a sensor for sensing a quality of air or gas in the system and may be adapted for activating or controlling the photocatalytic reactor as function of a sensed quality of air or gas in the system.

The present invention furthermore relates to the use of a photocatalytic reactor as described above for air or gas purification in a heating, ventilation and/or air conditioning system.

The present invention also relates to a method of updating a heating, ventilation and/or air conditioning system, the method comprising replacing a section of the heating, ventilation and/or air conditioning system by a photocatalytic reactor as described above. It is an advantage of embodiments of the present invention that upgrading or maintaining of a HVAC system can be done relatively easily, without the need for replacing the full HVAC system.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
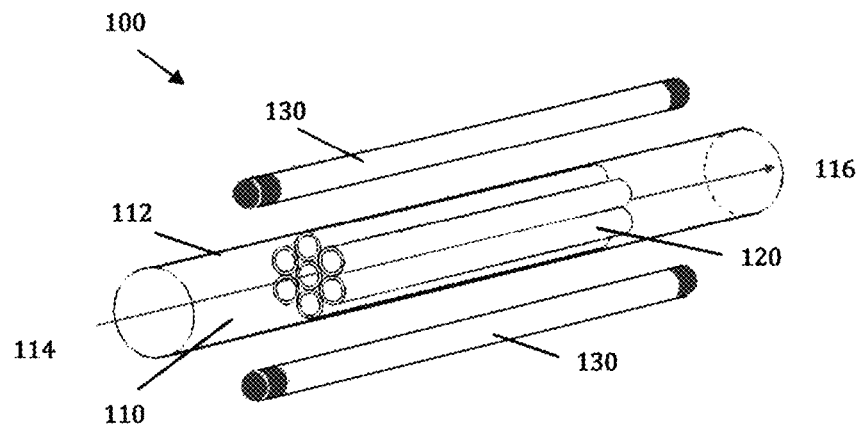
FIG. 1 illustrates a schematic representation of a photocatalytic reactor according to an embodiment of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings, but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In a first aspect, the present invention relates to a photocatalytic reactor for use in a heating, ventilation and/or air conditioning system. Heating, ventilation and/or conditioning systems are widely spread. They may be referred to as HVAC systems. As indicated above, photocatalytic oxidation typically is used for purification of air or gas in such systems. The photocatalytic reactor according to embodiments of the present invention comprises a longitudinal housing having a wall and comprising an inlet and an outlet for allowing air or gas to pass through along the longitudinal direction of the longitudinal housing.

The system also comprises a plurality of tubes positioned in the longitudinal housing and arranged such that some outer tubes are positioned closer to the housing wall than some inner tubes. The plurality of tubes having their longitudinal axis parallel with the longitudinal axis of the longitudinal housing allowing the air or gas to pass along and through said tubes. The tubes furthermore comprising photocatalytic material in or on their tube walls. The system furthermore comprises an irradiation system for irradiating the photocatalytic material for inducing catalytic action. The irradiation system and plurality of tubes are configured so that upon irradiating by the irradiation system photocatalytic material of said outer tubes as well as of said inner tubes is irradiated.

FIG. 1 illustrates a photocatalytic reactor 100 comprising a housing 110. The housing 110 has a wall 112 and has an inlet 114 and an outlet 116. The wall 112 of the housing 110 may be transparent, e.g. in case the irradiation source is positioned outside the housing, for the radiation of the irradiation sources used. FIG. 1 also shows an irradiation source 130, in the present example being two lamps. The irradiation source 130 may be a UV radiation source, such as for example a UV-A or UV-C source. It may be any type of irradiation source such as for example a tube-shaped irradiation source, a led strip, etc. Advantageously, the irradiation source may be elongated, such that it can irradiate the full length of the housing. Alternatively, or in addition thereto, also specific reflectors may be used for spreading the radiation along the housing. The reactor 100 also comprises a plurality of tubes 120, some outer tubes being positioned closer to the housing wall 112 than some inner tubes. The plurality of tubes 120 have their longitudinal axis parallel with the longitudinal axis of the longitudinal housing allowing the air or gas to pass along and through said tubes 120. The number of tubes may be at least 4 tubes, e.g. at least 7 tubes, e.g. at least more than 10 tubes. The tubes may be made of any suitable material, such as for example glass or quartz, like borosilicate, plastic, etc. The tubes typically comprise photocatalytic material. The photocatalytic material may be embedded in the tubes or may be provided at the outside and/or the inside of the tubes. It may be provided by coating, such as for example via dip coating or spray coating. The photocatalytic material may be any suitable photocatalytic material, such as for example $TiO_2$, $ZnO$, $Cu_xO$, $Fe_2O_3$, $CdS$, $GaP$, $ZnS$, $WO_3$, etc. Processes for applying the photocatalytic material as well as the chemical process of the photocatalytic action itself are well known in the field and therefore not being discussed here in detail anymore.

Advantageously, the plurality of tubes may be made of glass that is free or substantially free of sodium. Some examples thereof are borosilicate glass and quartz, which are mainly formed of silicondioxide ($SiO_2$).

Using sodium free glass also is especially advantageous for embodiments where the coating is applied to the glass tubes using a particular application technique. More particularly, in some embodiments, advantageously the coating, which for example may be titaniumdioxide ($TiO_2$), is applied to the tube, e.g. by dip coating or spray coating, and a calcination process is performed thereafter. The calcination process may be performed at a temperature of at least 400° C. or higher, e.g. at least 450° C. or higher, e.g. at least 500° C. or higher. The application process latter allows, especially in combination with the use of sodium free glass, in obtaining a good photocatalytic coating having good sticking properties with respect to the glass tube carriers. Without being bound by theory, the latter is expected to be caused by a binding between the photocatalytic material, e.g. $TiO_2$, and the silicon in the glass.

It is an advantage of embodiments of the present invention that the glass used is resistant to heat treatments at higher temperature, thus allowing to perform the calcination process during the formation of the coating on the glass tubes.

In some embodiments of the present invention the amount of photocatalytic material may be tuned so as to balance the photocatalytic activity with the activating radiation. The more photocatalytic material is present, the more the transmission of the activating radiation will be limited. The geometry applied, i.e. the position of the radiation sources with respect to the different tubes, also influences the amount of radiation absorption that is occurring by the photocatalytic material. The thickness as well as the geometry therefore may be adapted for optimizing the balance between photocatalytic activity and transmission of radiation.

Figure 11A:
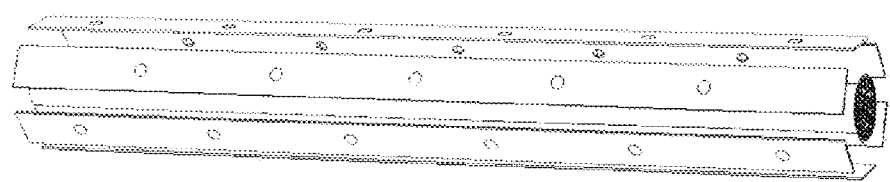
FIGS. 11(a) and 11(b) illustrate an elevated top view and cross-sectional view of an example of a reactor according to an embodiment of the present invention.
Figure 11B:
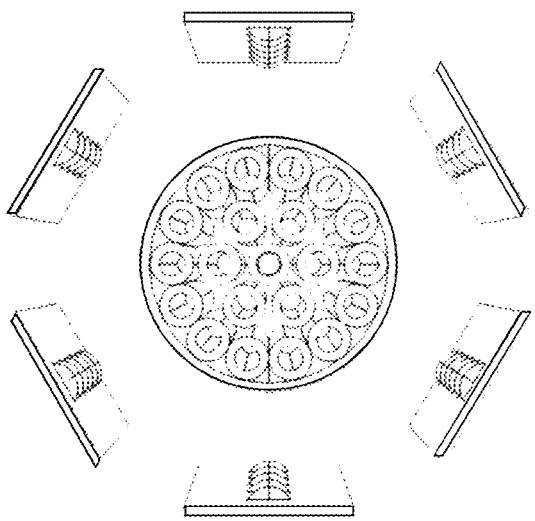
Figure 13:
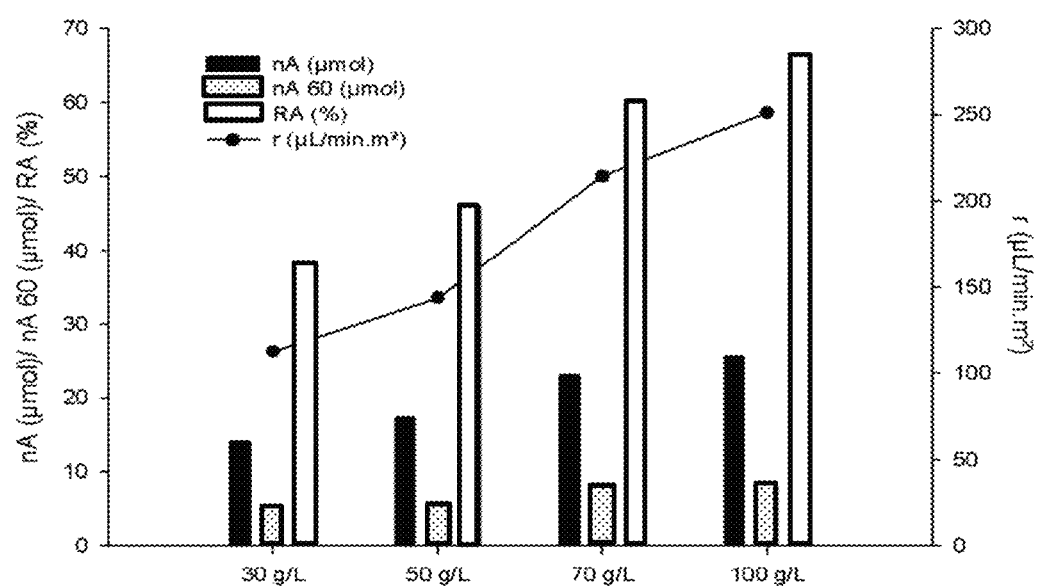
FIG. 13 and FIGS. 14(a) and 14(b) illustrate photocatalytic activity as function of the amount of photocatalytic material and the influence of transmission thereon, as can be used in embodiments of the present invention.
Figures 14A, 14B:
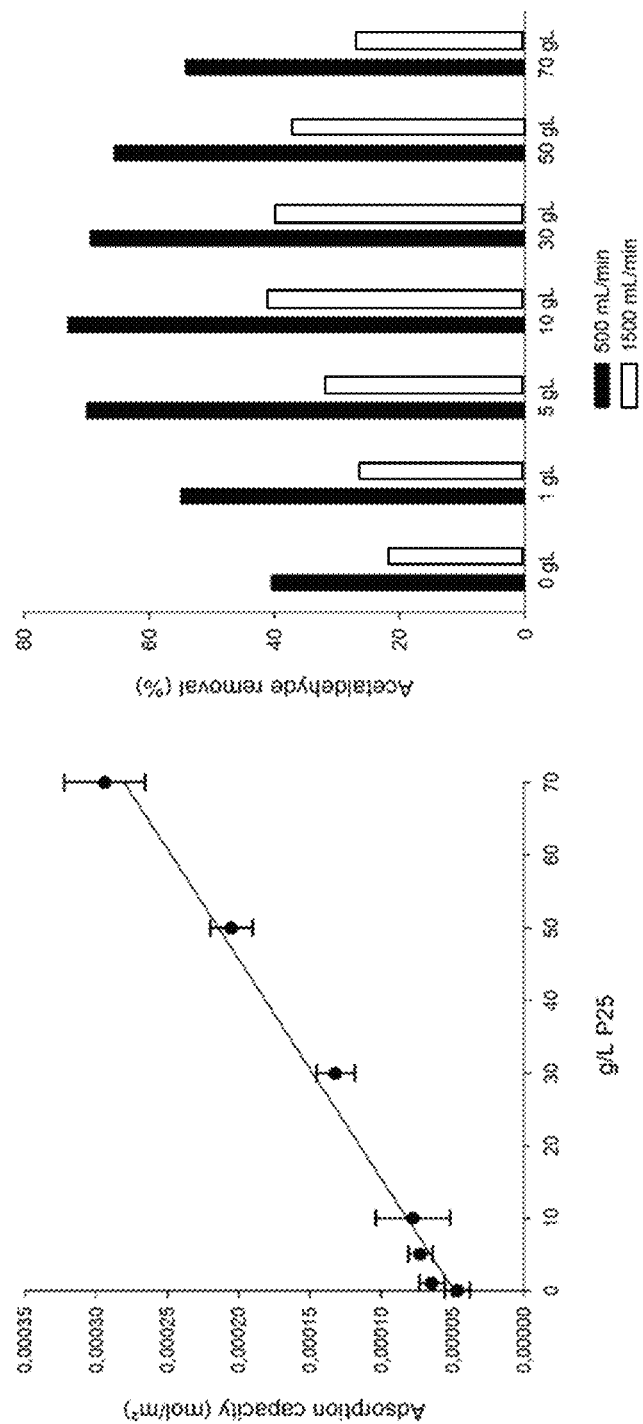

By way of illustration, the effect of photocatalytic activity as function of the amount of photocatalytic material is shown in FIG. 13. In the example shown titaniumdioxide is used, whereby the amount of titaniumdioxide is expressed in g/L per liter of sol-gel mixture. The titanium dioxide uses is commercially available titaniumdioxide P25. In FIG. 14(a), it is shown that the more titaniumdioxide is used, the more pollutants can be adsorbed by the coating. Nevertheless, the fact that a balance needs to be found is shown in FIG. 14(b), wherein a concentration of 10 g/L shows the best result for two different flow rates for a given complex geometry, and thus not the coating with a higher titaniumdioxide concentration. The latter is caused by the effect of absorption of the radiation. By way of illustration, embodiments of the present invention not being limited thereto FIG. 11(a) illustrates an elevated top view and FIG. 11(b) illustrates a cross-sectional view of a reactor according to an embodiment of the present invention. In the example shown, the irradiation sources used are led strips and the reactor comprises 21 tubes.

Figure 12A:
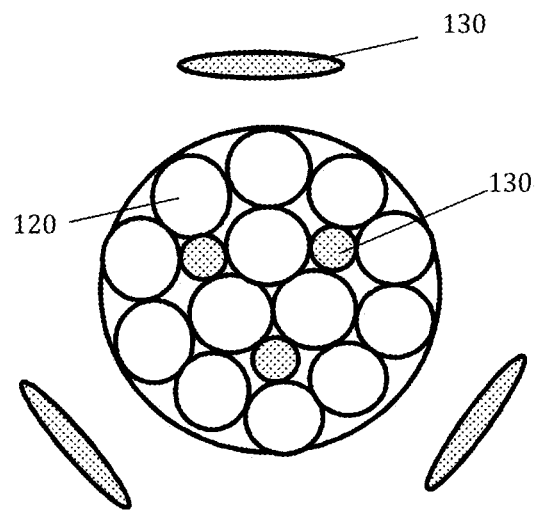
FIGS. 12(a) to 12(c) illustrate cross-sectional views of different reactors according to embodiments of the present invention.
Figure 12B:
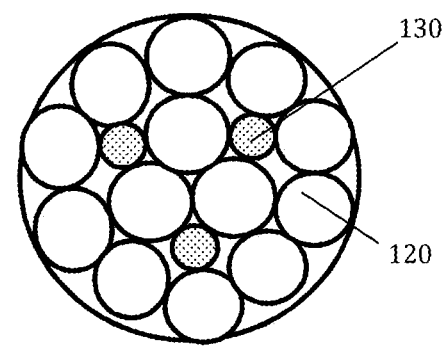
Figure 12C:
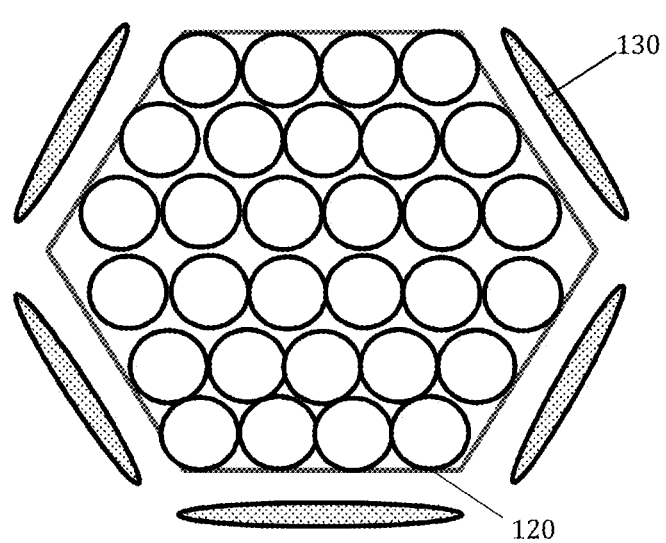

In FIGS. 12(a) to 12(c), cross-sections of further examples are shown. In FIG. 12(a) an example is shown with irradiation sources in between the tubes as well as outside the housing. In FIG. 12(b) an example is shown with irradiation sources solely in between the tubes and in FIG. 12(c) an example is shown with irradiation sources solely outside the housing. It is to be noticed that the total number of tubes, nor their cross-sectional shape is not limiting for embodiments of the present invention. Furthermore, it is to be noticed that the shape of the longitudinal housing is not limiting (e.g. circular cross-section, elliptical cross-section, polygonal shape, etc.).

In some embodiments, the tubes may be configured such that the outer sides of the tube form similar feedthroughs as the inner side of the tubes. It is to be noted that in some embodiments the tubes may be selected in cross-sectional shape and in arrangement, such that the average area of a cross-section in between the tubes (considering a cross-section perpendicular to the length direction of the tubes) substantially matches the average area of the cross-section in a tube. In other words, for a feed-through determined by a passageway formed by the outer side of tubes, the perpendicular cross-sectional area advantageously is within 20% to 180%, advantageously within 50% to 150%, e.g. within 80% to 120% of the average perpendicular cross-sectional area of a tube. Matching of the cross-sections allows for having a comparable pressure drop in the tubes and through the passageways outside the tubes. If the photocatalytic material is present both at the inner sides and the outer sides, the latter allows for more comparable treatment times and therefore for an efficient use of both tubes and feedthroughs in between the tubes.

Figure 15:
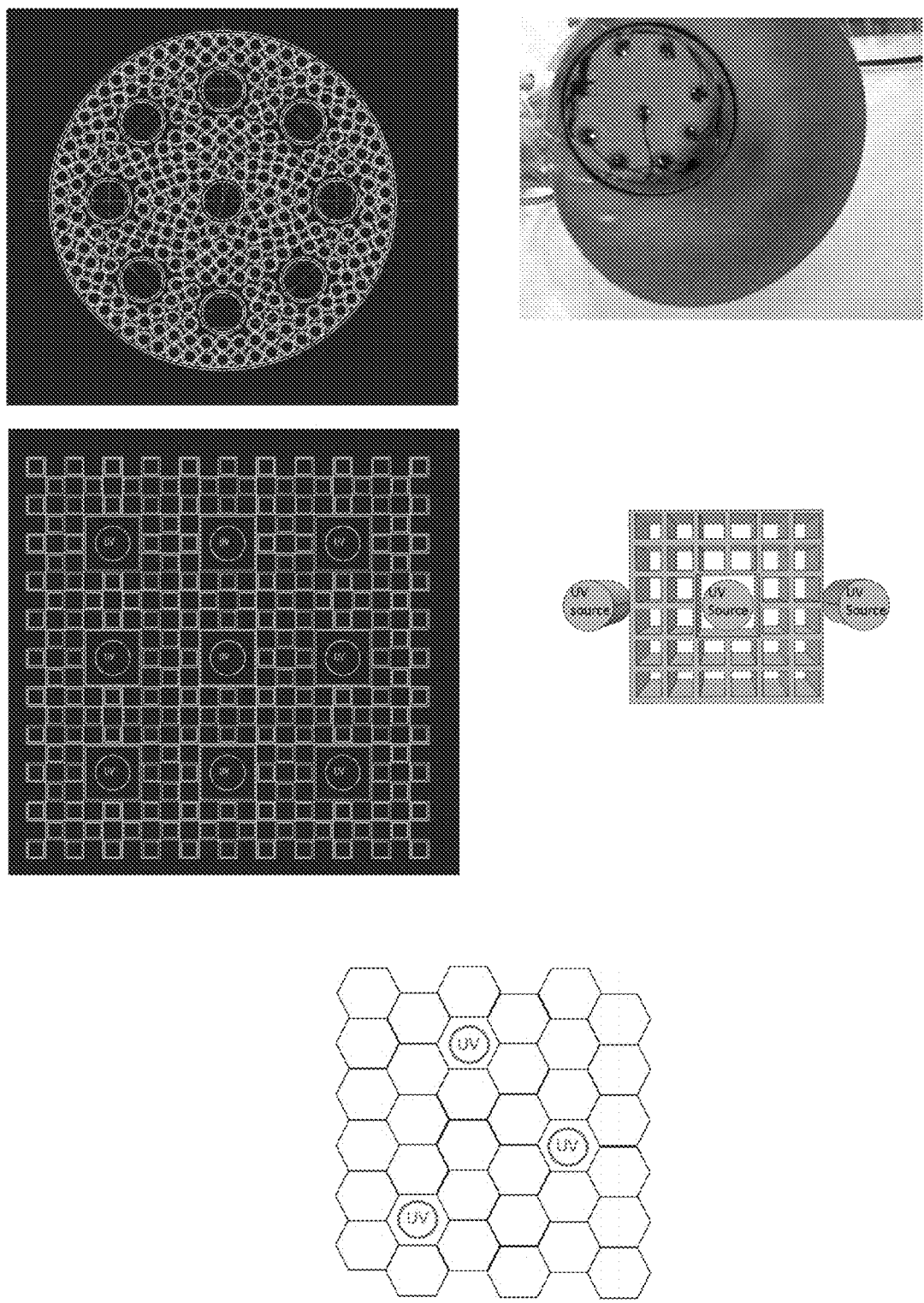
FIG. 15 illustrates possible shapes of tubes and geometrical design of the reactor, according to some embodiments of the present invention.

Some examples of specific shapes of the tubes can be seen in FIG. 15. In some embodiments, the tubular shaped passageways may be formed by a monolithic structure or semi-monolithic structure casted, printed or formed in any other way.

In some embodiments, systems may further comprise one or more additional filters, e.g. positioned prior to the photocatalytic reactor for adsorbing VOCs and possible additional substances. Once the filter is saturated, the captured component may be released (desorbed) (e.g. by applying heating through applying a voltage over the filter) and sent through the photocatalytic reactor until the pollutants are sufficiently cleaned. Simultaneously during this phase, another filter can at that time be used for capturing VOCs and possible additional substances of the incoming flow, which can be connected to the photocatalytic reactor once saturation of this other filter occurs. In this way, by alternatingly using the photocatalytic reactor for different filters, a continuous filtering process of an input flow can be guaranteed. One example of a filter that can be used is an active carbon-type filter. Such filters are well known in the art.

Further by way of illustration, embodiments of the present invention not being limited thereto, results are discussed illustrating features and advantages of the tube based photocatalytic reactors according to embodiments of the present invention.

Three candidate substrates were tested and compared: borosilicate glass tubes according to an embodiment of the present invention, borosilicate glass beads and glass fibers mats. The glass tubes had an internal diameter of 5, 7 and 9 mm and an external diameter of 7, 9 and 11 mm respectively; they are further described as 5ID7ED, 7ID9ED and 9ID11ED. Glass beads of two sizes (diameter 14 mm and 16 mm) were used. Commercial glass fibers mats were selected (Profil, 2.PS3"B.050) consisting of fibers with a thickness of (36±7) µm, determined by at least 30 thickness measurements of different fibers by optical microscopy. They form a structure with large open pores and their density can be adapted by compression. Glass fibers with three different densities (0.0054 g/cm³, 0.0090 g/cm³ and 0.0124 g/cm³) were used in this study.

Figure 2:
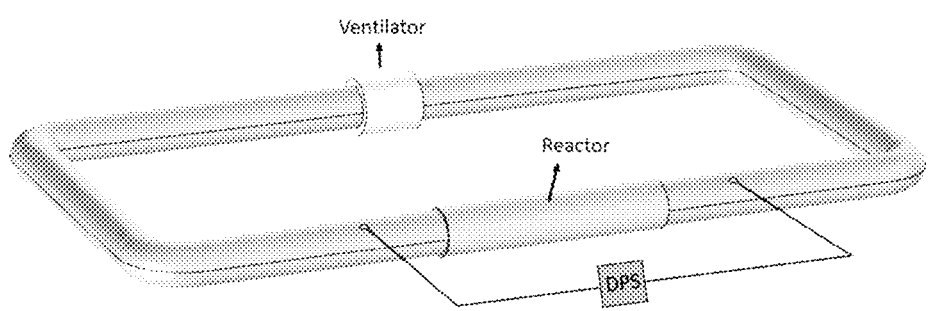
FIG. 2 illustrates a ventilation system with a photocatalytic reactor and differential pressure sensor, as can be used for testing pressure drop and for illustrating features and advantages of embodiments according to the present invention.

In a first experiment, pressure loss and permeability were tested. Pressure losses over the three substrates were measured and compared in a reactor integrated in a closed-circuit air duct system as shown in FIG. 2. The setup consisted of circular pipes (inner diameter 10.3 cm) with a total length of 600 cm. Air movement was created by a controllable inline duct fan which could induce wind speeds varying from 1.14 m/s to 4.4 m/s (for an empty reactor). The fan curve (pressure difference over the fan versus flow rate) was provided by the manufacturer. The reactor section consisted of a transparent pipe (length 54.5 cm, inner diameter 11.4 cm) that was fitted in the closed circuit. To compare the substrates, the reactor was partially (over a length of 20 cm) filled with glass tubes, glass beads or glass fibers and the pressure drop was measured by a differential pressure sensor (DPS) consisting of a pressure module (Fluke 717 30G, Fluke Corp.) with a range of −83 to 206.84 kPa and a pressure calibrator (Fluke 700PD2, Fluke Corp.). To keep the glass beads packed in the reactor, sparse polylactid acid grids (created with a 3D printer) were used on both sides of the beads. The presence of the grids required a correction for the additional pressure drop. Air flow rate was measured before the reactor inlet by a hotwire air velocity sensor (CTV 110, KIMO instruments).

In order to quantitatively compare the 'openness' of the substrates, measurements of the pressure drop were performed at a range of wind speeds depending on the flow resistance of the substrate (determined by the fan curve of the duct fan) and the experimental results were correlated to the Darcy-Forchheimer law by regression to obtain their permeability κ (m²). Darcy's law is a simple proportional relationship between the instantaneous discharge rate for a single-phase flow in a porous medium; in the Darcy-Forchheimer law, the Forchheimer term accounts for the non-linear behavior (influence of kinetic energy and inertia) of the pressure drop as a function of flow speed:

$$\frac{\Delta P}{\Delta x} = -\frac{\mu}{\kappa} \times q - \frac{(\rho \times q^2)}{\kappa_1}$$

with ΔP the pressure drop (Pa), Δx the length of the substrate in the flow direction (m), µ the viscosity of the flow (Pa·s), q the flow speed (m/s), ρ the density (kg/m³) and $\kappa_1$ the inertial permeability (m).

The exposed surface area of the three substrates was determined from simple geometrical calculations, considering the densest packing of tubes or beads. A reactor filled with 5ID7ED, 7ID9ED and 9ID11ED glass tubes resulted in respectively 190, 113 and 77 tubes in the reactor, with a corresponding surface area of 75.4, 100.53 and 125.66 cm² respectively (both inner and outer surface are included in the exposed surface area). In case of glass beads, the densest packing corresponded to 513 beads (16 mm diameter) and 819 beads (14 mm diameter). The surface area of glass fibers was calculated from the weight, the density of glass (2.5 g/cm³) and the fiber thickness of 36±7 µm, determined by 30 optical microscopy measurements.

In table 1, the permeability, calculated using the Darcy-Forcheimer law, and the exposed surface area of the studied substrates are shown. As mentioned, a suitable substrate combines a high permeability to minimize the energy consumption with a large exposed surface area available for coating.

TABLE 1

| Substrate | Permeability K (m$^2$) | Exposed surface area (cm$^2$/cm$^3$) |
|---|---|---|
| Glass fibers (0.0124 g/cm$^3$) | 2.18 10$^{-7}$ | 4.95 |
| Glass fibers (0.009 g/cm$^3$) | 3.34 10$^{-7}$ | 3.56 |
| Glass fibers (0.0054 g/cm$^3$) | 7.36 10$^{-7}$ | 2.14 |
| Glass beads (14 mm diameter) | 1.76 10$^{-8}$ | 2.21 |
| Glass beads (16 mm diameter) | 6.84 10$^{-8}$ | 1.81 |
| Glass tubes (5ID7ED) | 5.82 10$^{-7}$ | 7.02 |
| Glass tubes (7ID9ED) | 9.14 10$^{-7}$ | 5.57 |
| Glass tubes (9ID11ED) | 1.36 10$^{-6}$ | 4.74 |

Figure 3:
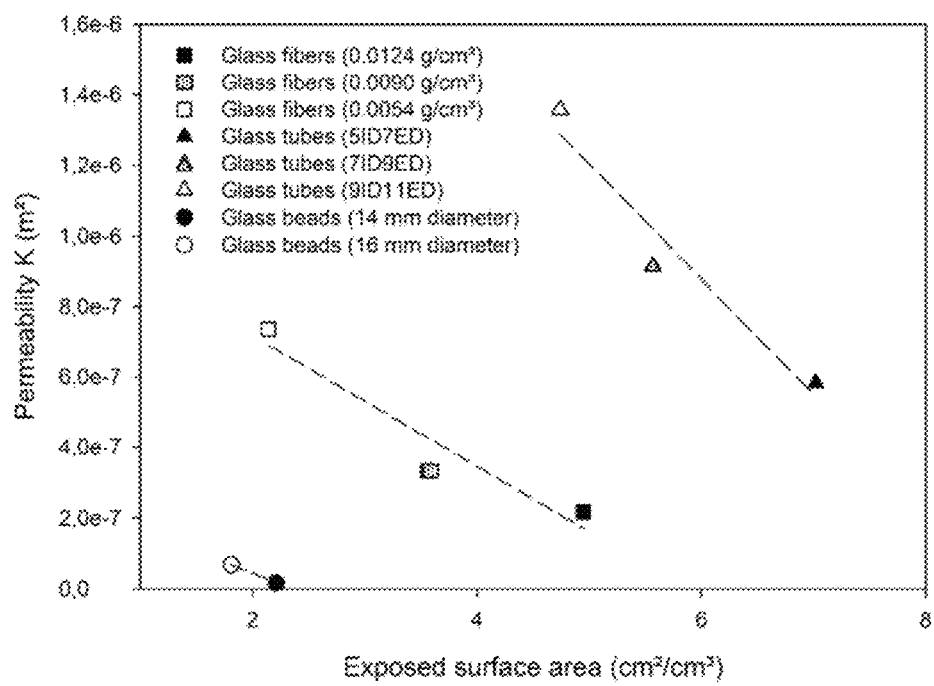
FIG. 3 illustrates the permeability K plotted against the exposed surface area for different types of substrates, illustrating features and advantages of embodiments according to the present invention.

A plot of the exposed surface area against the permeability is shown in FIG. 3. The most suitable substrate is located in the right upper corner of the figure, where the highest permeability and exposed surface area are combined. For each type of substrate, a trade-off exists between these two vital criteria as illustrated by the dashed trend lines plotted in FIG. 3. The glass tubes scored best on both criteria which makes them the most suitable substrate for the application. Even though glass beads with large diameters were used to minimize the pressure drop, their permeability was still very low compared to the other substrates. Besides, their exposed surface area was relatively low. The glass fibers showed a moderate performance on both permeability and exposed surface area.

With the fan used in the experimental setup described in FIG. 2, one could only reach a maximum air speed of 4.4 m/s for an empty reactor. In the ducts of a ventilation system, air speeds of up to 7 m/s are no exception. To further characterize glass tubes in terms of their airflow resistance properties at more realistic (higher) air speeds, a modelling approach was used. An additional advantage of modelling is that also geometrical effects (other lengths and diameters of tubes) can easily be studied. The commercial software package Comsol Multiphysics v5.2a was used to perform computational fluid dynamics (CFD) simulations in the setup shown in FIG. 2.

Figure 4:
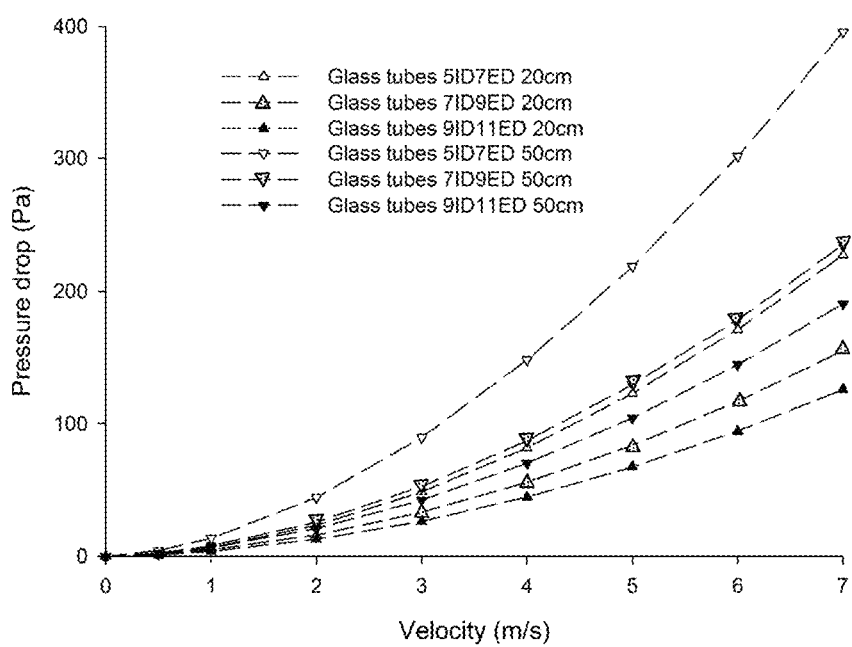
FIG. 4 illustrates the pressure drop for real velocities, illustrating features of embodiments according to the present invention.

FIG. 4 shows the pressure drop corresponding to 3 configurations of glass tubes (5ID7ED, 7ID9ED and 9ID11ED) as calculated by the Comsol model. The reported pressure drops are the modeled pressure differences between the actual locations of the DPS. Results are given for a completely stacked reactor, for air velocities ranging from 1 to 7 m/s (air velocity at the anemometer position). For each type of glass tubes, two glass tube lengths were considered: 20 and 50 cm. As a practical guideline based on energy consumption considerations, a threshold of 200 Pa was set for the additional pressure drop, caused by the reactor. All configurations of 20 cm length fulfil this requirement, except for 5ID7ED at a velocity of 7 m/s. For a reactor length of 50 cm, only the pressure loss corresponding to the largest diameter of tubes (9ID11ED) remains below the set point. Obviously, the aerodynamic entry length (where the flow is developing) causes most of the pressure drop. The entry length depends on the flow characteristics (the Reynolds number) and the tube diameter. For many turbulent pipe or tube flows, the entry length is approximated as:

$$L=1.359 Re^{1/4}$$

As can be seen from the results, the pressure drop per unit length corresponding to tubes of 20 cm is at least a factor 1.45 higher than for tubes of 50 cm. From this point of view, it is better to extend the length of the reactor rather than using smaller tubes.

In some experiments, the photocatalytic coating was evaluated. Obviously, the photocatalytic coating is a significant and determining component of a PCO reactor. Considering the installation, maintenance and operating conditions (e.g. high wind speeds) of ventilation systems, excellent coating adhesion of the photocatalyst is also vital. In the present example a dip-coating method with P25 based powder-modified sol-gel was used and obtained excellent adhesion and good photocatalytic properties for borosilicate glass were obtained. A range of concentrations of P25 to compare adhesion properties and photocatalytic activity. The glass tubes were dip-coated with a fixed withdrawal speed of 120 mm/min in P25 based powder-modified sol-gels and afterwards dried in the oven at 90° C. for 24 hours. The modified sol-gels consisted of a 0.5 M solution of commercial titanium isopropoxide (TTIP, 97%, Aldrich), isopropanol (i-PrOH, Sigma-Aldrich) and diethanolamine (DEA, Sigma-Aldrich) (with a DEA/TTIP molar ratio of 4 and a H$_2$O/TTIP molar ratio of 2) and P25 TiO$_2$ (Evonik) at seven different concentrations: 0 g/L, 1 g/L, 5 g/L, 10 g/L, 30 g/L, 50 g/L and 70 g/L. The coating procedure required a subsequent calcination step at 500° C.

For each coating, the adhesion of catalyst particles to the substrate was evaluated by means of the classic Scotch Tape Test, and by submitting the coated substrate to parallel compressed airflow, corresponding to a wind speed of at least 13 m/s as measured by a hotwire air velocity sensor (CTV 110, KIMO instruments) while monitoring the amount of released nanoparticles, using an ultrafine particle counter (P-trak, TSI systems).

For each P25 loaded sol-gel coating, the amount of released nanoparticles under compressed airflow equaled the background measurement. This proves that the coating is suitable for the operating conditions of a ventilation system in which high air flow velocities are typical. 0 g/L, 1 g/L, 5 g/L, 10 g/L, 30 g/L, 50 g/L P25 coatings passed the Scotch Tape Test. For the 70 g/L P25 coating, a small amount of white titanium dioxide particles was released on the tape and the 100 g/L P25 coating completely failed the test, rendering it useless for the application.

In further experiments, the photocatalytic activity of the coating was also evaluated.

Figure 5:
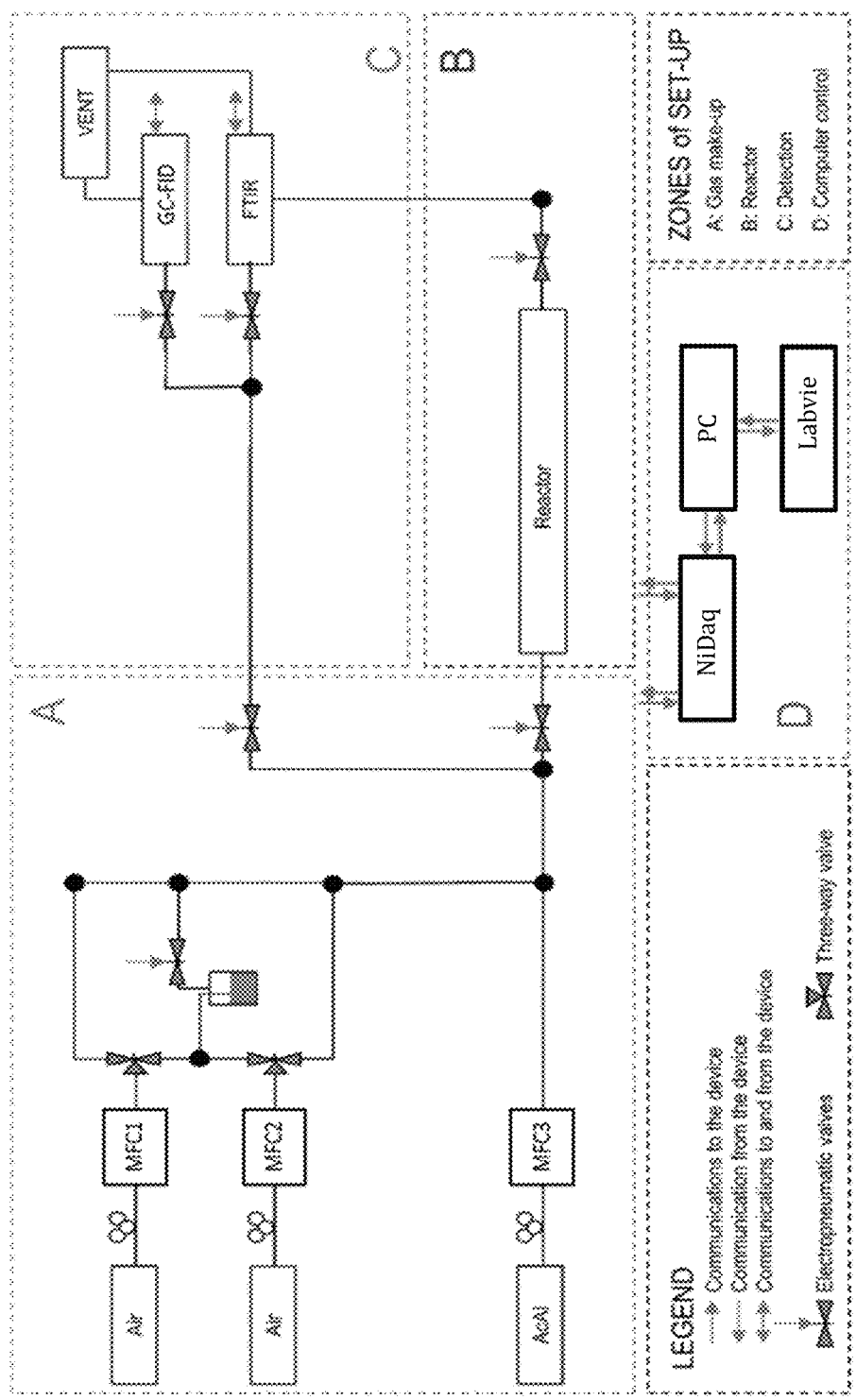
FIG. 5 illustrates a full reactor test-setup for evaluating photocatalytic activity, as can be used in experiments for testing properties of systems according to embodiments of the present invention.

The photocatalytic activities of the seven P25 based powder-modified sol-gels were tested according to ISO 22197-2:2011, a standard performance test method of semi-conductive photocatalytic materials for the removal of acetaldehyde in air. The experiments were performed with a fully automated setup which is shown in FIG. 5. Acetaldehyde (Messer, 1% in N2) was mixed with synthetic clean air (Messer) using two independent mass flow controllers (MFC1 & MCF2) with a fixed total flow rate of 1000 cm$^3$/min for synthetic air and one mass flow controller (MFC3) with a fixed flow rate of 2 cm$^3$/min for the contaminant, resulting in a stable continuous flow of 5 ppmv acetaldehyde. MFC2 was coupled to a temperature-controlled gas wash to obtain a specified relative humidity of 50%. The reactor can be by-passed using pneumatic valves to force the contaminated gas flow directly to the measurement devices. The outlet acetaldehyde concentration was measured every 4 minutes using a CompactGC 4.0 analyser (Interscience) equipped with a flame ionization detector (FID).

The photocatalytic ISO standard reactor was made from stainless steel, which is inert with regard to acetaldehyde and UV light. The test samples were illuminated through a quartz glass window resulting in an incident UV (300-400 nm) intensity of 10 W/m$^2$. The contaminated gas stream flowed from inlet to outlet, through a gap of 5 cm between the quartz window and test samples. Prior to each photocatalytic experiment, the samples were pretreated for 24 hours with UVA light of an incident light intensity of 15 W/m² to remove all organic residues. Borosilicate test samples (glass plates 20 cm length and 10 cm width) were coated using the modified sol-gel method with 4 different concentrations of P25, i.e. 30 g/L, 50 g/L, 70 g/L and 100 g/L.

The photocatalytic activities of the coatings were expressed and compared by common-used expressions from the literature: the removal percentage of acetaldehyde $R_A$ [%], the quantity of acetaldehyde removed during the whole experiment $n_A$ [μmol], the quantity of acetaldehyde removed during the last hour of the experiment $n_A(60)$ [μmol] and the photocatalytic rate per unit area r [μL/min·m²], given by the following equations.

$$R_A = \frac{\phi_{AO} - \phi_A}{\phi_{AO}} \times 100$$

$$n_A = \left(\frac{60f}{22.4}\right) \times B$$

$$n_A(60) = \left(\frac{60f}{22.4}\right) \times (\phi_{AO} - \phi_A)$$

$$r = \frac{\phi_{AO} \times f}{S} \times LN\left(\frac{1}{1 - \frac{\phi_A}{\phi_{AO}}}\right)$$

where $\phi_{AO}$ is the supply volume fraction of acetaldehyde [ppm], $\phi_A$ the volume fraction of acetaldehyde at the reactor outlet [ppm], f the flow rate of test gas [L/min], B the amount of acetaldehyde removed [ppm/h] and S the surface area of the sample exposed to light [m²]. It should be stressed that in a complex reactor geometry, there are several effects besides the photocatalytic efficiency of the coating that can influence the photocatalytic conversion and the reactor performance, including mass transfer (diffusion and advection) and light distribution. The tests in the ISO standard reactor were done to exclude these effects and thus to be able to focus on the photocatalytic activity of the coating itself.

TABLE 2

| Parameters | 30 g/L | 50 g/L | 70 g/L | 100 g/L |
|---|---|---|---|---|
| nA (μmol) | 14.13 | 17.46 | 23.10 | 25.61 |
| nA 60 (μmol) | 4.79 | 5.76 | 7.54 | 8.23 |
| RA (%) | 37.93 | 45.89 | 59.82 | 66.07 |
| r (μL/min · m²) | 112.45 | 143.85 | 214.62 | 251.28 |

Figure 6:
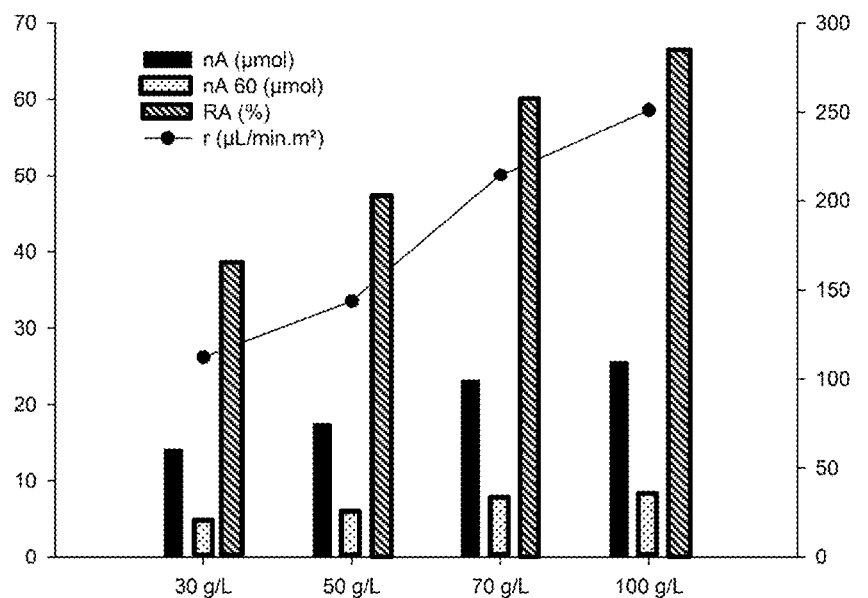
FIG. 6 illustrates a quantitative comparison of the photocatalytic activity, as can be used for evaluating systems according to embodiments of the present invention.

Table 2 and FIG. 6 show a quantitatively comparison of the photocatalytic activity for 4 different P25 loaded sol-gel coatings (30 g/L, 50 g/L, 50 g/L and 100 g/L). An obvious conclusion is that the more P25 is added to the modified sol-gel, the more photocatalytic conversion is achieved according to all evaluating criteria (i.e. the removal percentage of acetaldehyde $R_A$, the quantity of acetaldehyde removed during the whole experiment $n_A$, the quantity of acetaldehyde removed during the last hour of the experiment $n_A(60)$ and the photocatalytic rate per unit area r). Secondly, the quantity of acetaldehyde removed during the last hour $n_A(60)$ is for all P25 loadings more or less a third of the total quantity of acetaldehyde removed during the whole experiment of 3 hours. This indicates that the photocatalytic conversion is very stable from the moment that the UV-A light is switched on. Based on FIG. 6, the 100 g/L P25 modified sol-gel coating performs best. It is to be emphasized that in a realistic reactor geometry, several factors other than the coating activity may affect the efficiency and performance of the system. In the ISO standard reactor, light is uniformly distributed and the light intensity is sufficient for the photocatalytic reaction to proceed.

Yet a further experiment focused on reactor design and the light intensity distribution therein.

A laboratory scale PCO reactor was constructed from glass tubes as shown in FIG. 1. The reactor consisted of a borosilicate glass tube with an internal diameter of 29 mm and a length of 44 cm, provided with inlet and outlet connections (diameter 4 mm) perpendicular to its longitudinal axis and a closing mechanism using butyl rubbers to seal both ends airtight. The test reactor was symmetrically filled with 7 coated glass tubes (7ID9ED) to from a 'parallel flow tube reactor'. Two 25 W UV-A lamps were positioned on opposite sides and parallel to the reactor, at a distance from the reactor and resulting in an incident intensity on both outer surfaces of the reactor of 2.1 mW cm⁻², as measured by a calibrated Avantes Avaspec-3648 spectrometer.

Figure 7:
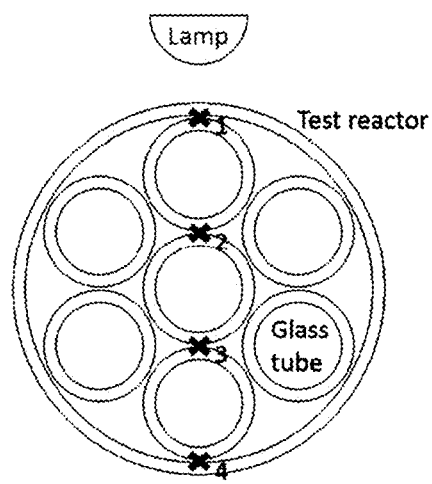
FIG. 7 illustrates a light intensity measurement setup at 4 fixed positions as performed for evaluating a system according to an embodiment of the present invention.

Light intensity and uniformity are among the critical performance parameters of a PCO reactor, especially when high airflow rates are involved. 'Dark spots' should be avoided as they can severely limit the photocatalytic conversion efficiency. Light intensity and uniformity are determined by the light source but also by the properties of the substrate and the coating. A calibrated Avantes Avaspec-3648 spectrometer was used to measure the emitted spectral UV light intensity at several positions in the parallel flow tube reactor. The light intensity measurements were integrated over the emitted spectral range (between 300 and 400 nm and a peak at 367 nm). For the light intensity measurements, only one 25 W UVA lamp (Philips) was used, positioned above and parallel to the reactor at a distance of 7 mm from the reactor. Based on the configuration of the glass tubes (7ID9ED), 4 incident light intensity measurement positions were defined, as shown in FIG. 7. Measurements were performed for uncoated tubes and for tubes coated with modified sol-gels prepared with α different concentrations of P25: 1, 5, 10, 30, 50 and 70 g/L. Each measurement was done with the sensor surface oriented perpendicular to the light source to measure the UV light extinction while travelling through different layers of tubes and coatings.

Figure 8:
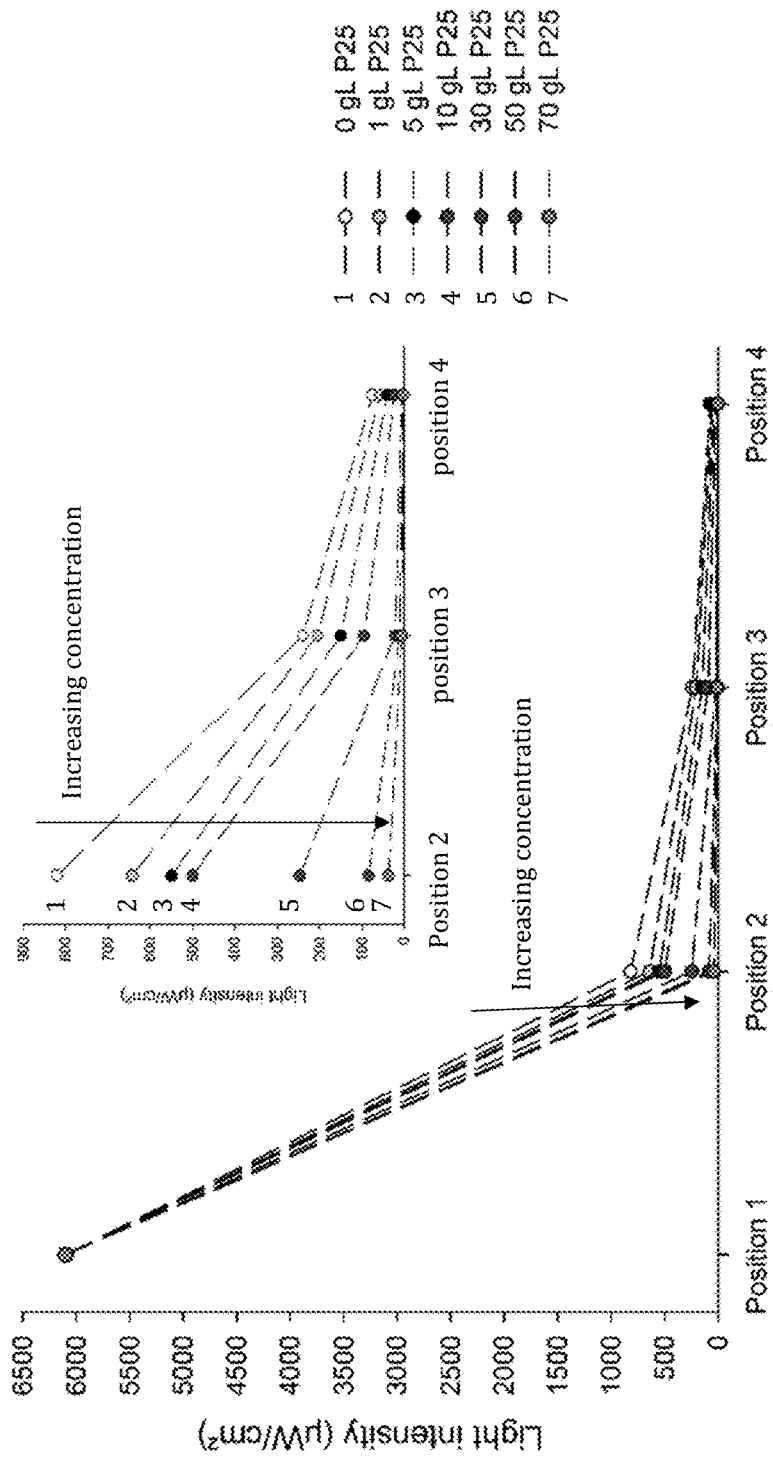
FIG. 8 illustrates light intensity measurements as obtained using a system as shown in FIG. 7.

UV-A measurements were performed for all P25 loaded sol-gel coated 7ID9ED tubes in the parallel flow tube reactor and the results are given in Table 3 and FIG. 8. The UV-A (300-400 nm) light intensity measured directly on the surface of the lamp was 120 000 μW/cm². At position 1 (FIG. 7), right behind the borosilicate reactor wall (>95% UV-A transmission), a UV-A light intensity of 61 000 μW/cm² was measured. According to the results given in Table 3, a drastic reduction of light intensity is observed from position 1 to position 2. Over 90% (for the highest P25 loaded coating even 99.5%) of the light did not pass the first coated tube. The light extinction is due to reflection, refraction and absorption and clearly depends on the amount of P25 used to prepare the coating. At position 4 (after 3 layers of tubes), the light emitted by the UV-A lamp is completely extinct for all coatings. The results indicate that light transmission is an important design parameter and should be optimized to avoid 'dark spots'. The latter would permit harmful VOC molecules to pass through the reactor without being removed by photocatalysis. Even though the UV light drastically decreases while travelling through the solid parts of the reactor, a significant improvement can be made by appropriate and thoughtful design (e.g. the quantity, type and positions) of the UV sources.

TABLE 3

| Pos | 0 g/L ($\mu W/cm^2$) | 1 g/L ($\mu W/cm^2$) | 5 g/L ($\mu W/cm^2$) | 10 g/L ($\mu W/cm^2$) | 30 g/L ($\mu W/cm^2$) | 50 g/L ($\mu W/cm^2$) | 70 g/L ($\mu W/cm^2$) |
|---|---|---|---|---|---|---|---|
| 1 | 6100 | 6100 | 6100 | 6100 | 6100 | 6100 | 6100 |
| 2 | 820 | 642 | 550 | 500 | 247 | 84 | 37 |
| 3 | 240 | 205 | 150 | 95 | 22 | 11 | 6 |
| 4 | 75 | 57 | 40 | 23 | 6 | 3 | 2 |

Finally, experiments also were performed on reactor performance. To evaluate the parallel flow tube reactor concept, activity measurements were performed with coatings prepared from 7 different P25 loadings (0, 1, 5, 10, 30, 50 and 70 g/L P25) and at two fixed inlet air velocities. Hereto, acetaldehyde (Messer, 1% in $N_2$) was mixed with synthetic clean air (Messer) using the fully automated test setup at a fixed total flow rate of 500 and 1500 $cm^3$/min. In this case, the outlet acetaldehyde concentration was measured using online FTIR spectroscopy by means of the IR peak height at 2728 $cm^{-1}$, corresponding to the v(C—H) stretch vibration. Prior to these performance experiments, the coated substrates were irradiated by UV light for 24 hours in order to clean all organic rest fractions from the $TiO_2$ surface. These experiments were carried out using two 25 W UV-A lamps. Activity experiments were performed in four phases: (1) 15 minutes in by-pass mode during which the gas flow is sent directly to the FTIR detection cell without passing through the reactor, in order to determine the initial concentration level of acetaldehyde, (2) 180 minutes of adsorption phase where the gas flows through the reactor in dark conditions in order to achieve adsorption-desorption equilibrium, (3) 90 minutes gas flow through the reactor under UV-A illumination to trigger photocatalytic reactions and (4) another adsorption phase to re-establish the adsorption/desorption equilibrium.

Figure 9:
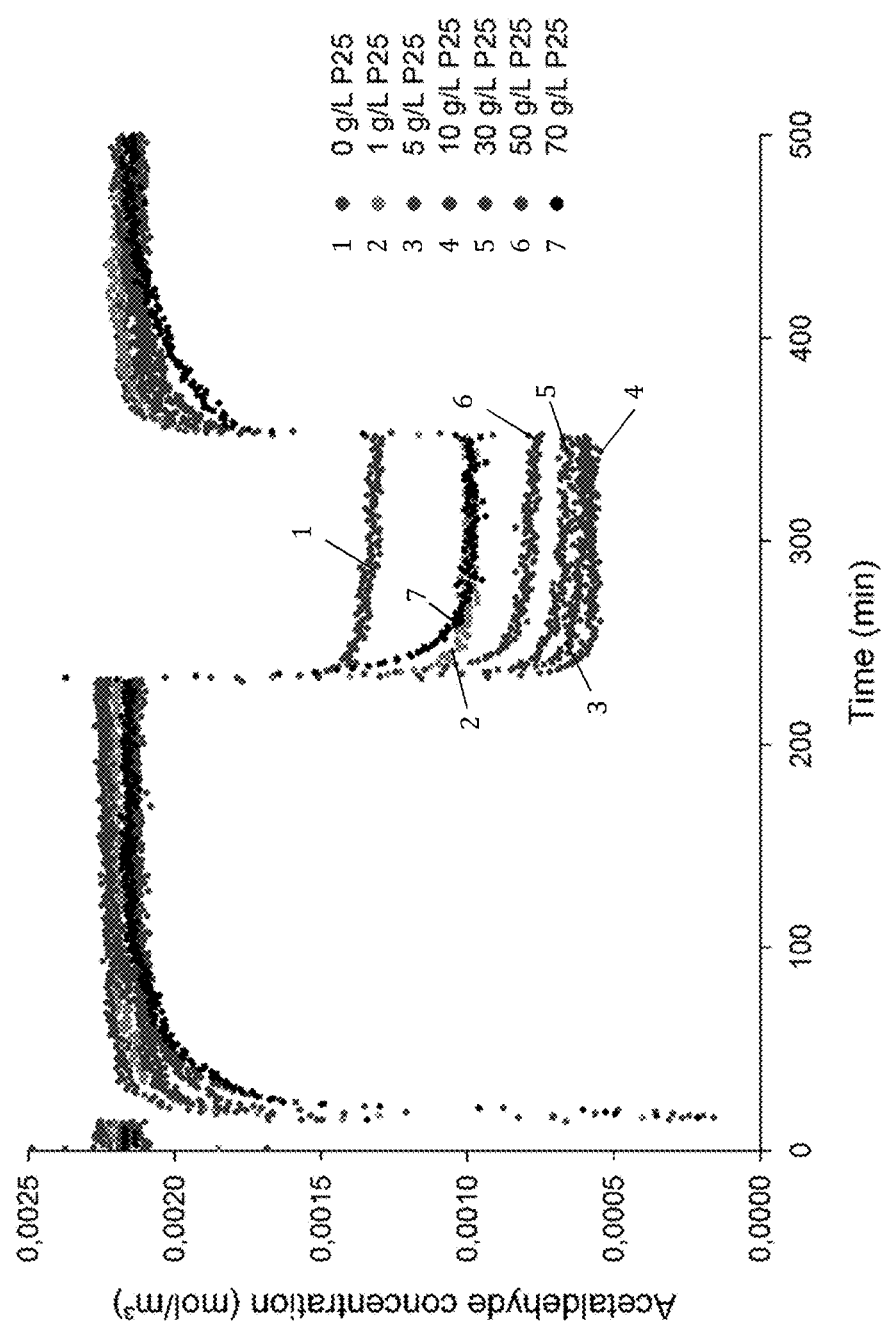
FIG. 9 illustrates a comparison of photocatalytic degradation for coatings with different composition, illustrating advantages of embodiments according to the present invention.
Figure 10:
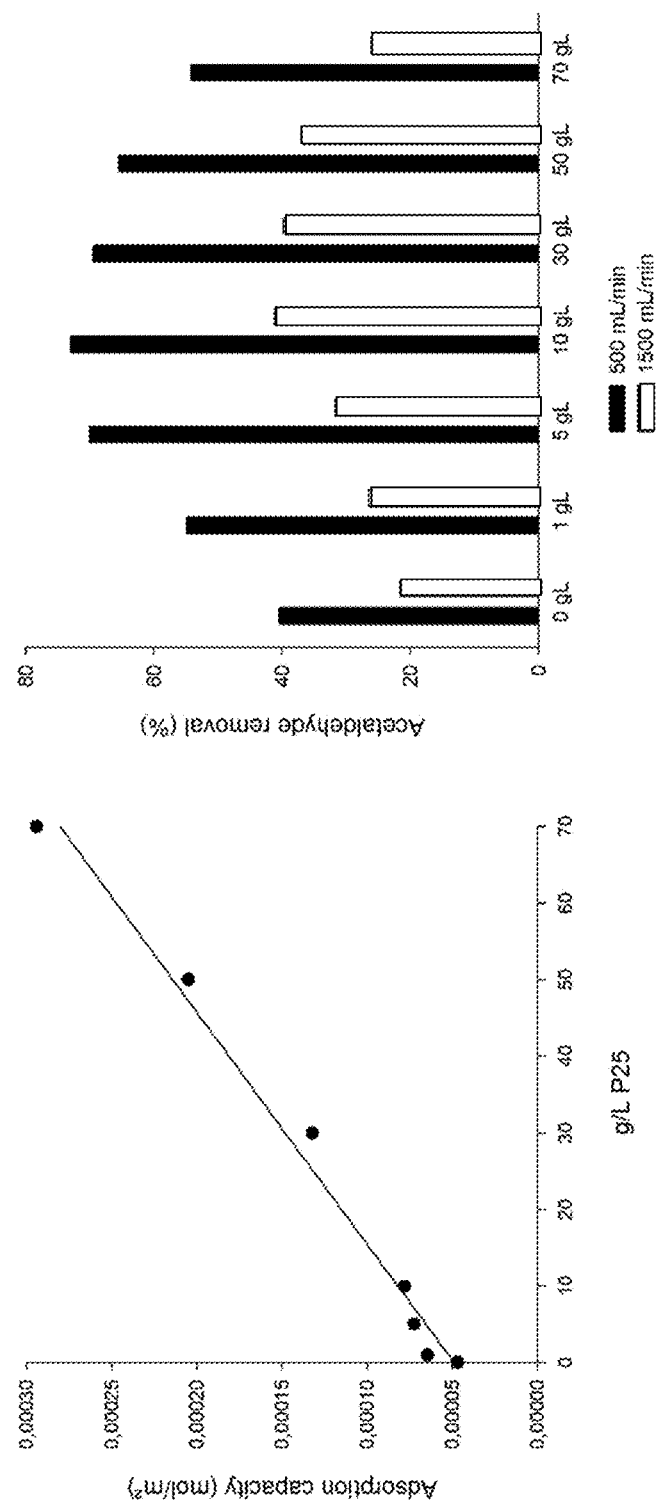
FIG. 10 illustrates the adsorption capacity of systems (left hand side) and the photocatalytic conversion of acetaldehyde (right hand side), as can be obtained using embodiments of the present invention.

The acetaldehyde adsorption capacities of the 7 sets of coatings at equilibrium were derived by integrating the non-steady-state acetaldehyde concentration over time during the adsorption phase and subtracting the obtained values from the amount of acetaldehyde entering the reactor during the same period. A correction was made for the dead space in the reactor by performing the same experiments with 7 uncoated glass tubes at the same fixed flow rate and bulk acetaldehyde concentration. For every experiment, the acetaldehyde removal (%) was derived by the ratio of the steady-state acetaldehyde concentration in phase 3 (UV-A illuminated conditions) to the steady-state acetaldehyde concentration in phase 1. FIG. 9 shows the acetaldehyde concentration profiles at the parallel flow tube reactor using online FTIR spectroscopy at a fixed flow rate of 500 mL/min during the four phases of the experiment (by-pass, adsorption, photocatalytic and second adsorption phase), for the parallel flow tube reactor built with 7ID9ED tubes. Similar experiments (at the same acetaldehyde inlet concentration) were performed for a flow rate of 1500 mL/min (results not shown). The average acetaldehyde inlet concentration was derived from the by-pass phase for each experiment as $(2.19\pm0.05)\times10^{-3}$ $mol/m^3$. Variations of the inlet concentrations were due to the inaccuracy of the mass flow controllers. In FIG. 10a, the adsorption capacity (an indication of the amount of active sites of the photocatalyst) for all coated set of tubes is shown. These values were derived by integrating the acetaldehyde concentration over time during the adsorption phase and subtracting the obtained values from the amount of acetaldehyde entering the reactor in during the same period, while correcting for reactor dead space. The adsorption capacity of the coated tubes increased linearly with the amount of P25 used to prepare the sol-gel ($R^2$=0.985). FIG. 10b shows the acetaldehyde removal capacity of the parallel flow reactor for both flow rates, 500 and 1500 mL/min. Despite the high adsorption capacity of the 70 g/L sol-gel coating and despite the fact that the photocatalytic reaction occurs from adsorbed acetaldehyde molecules, the highest removal capacity was observed for the reactor containing 10 g/L P25 coated glass tubes. For this coating, acetaldehyde removal capacity was 72.9% and 41.1% for 500 and 1500 mL/min flow rate respectively. The results are contrary to the previous findings (4.2.2 Photocatalytic activity of the coating) where more P25 resulted in higher photocatalytic activity, even though in the laboratory scale parallel flow tube reactor, two fluorescent UV-A lamps were used to illuminate 7 tubes. Clearly, the opposing effects of increasing the P25 load on the activity and the light transmission should be accounted for in the design of an efficient PCO reactor, parallel flow tube reactor or others and one should always compromise between photocatalytic activity and UV-A light transmission. This implicates that different geometries and different light source configurations will result in different coating optimums and therefore an in-depth case by case investigation is required in order to design, optimize and upscale parallel flow tube reactors for photocatalytic air purification. An efficient reactor should have a high degradation efficiency, a high UV-A light transmission and a low pressure drop, in a physically compact vessel.

In a second aspect, the present invention relates to a heating, ventilation and/or air conditioning system (HVAC) comprising a photocatalytic reactor as described in the first aspect. In some embodiments, a system is provided wherein sensing elements are provided for detecting the quality of the air or gas in the system. The photocatalytic reactor may be activated or controlled as function of the sensed quality of the air or gas in the system. Such control can be for example done by activating or dimming the irradiation sources or only use a part of the irradiation sources present.

Features and advantages as described in the first aspect may apply mutates mutandis for such a heating, ventilation and/or air condition system (HVAC).

In a third aspect, the present invention also relates to the use of a photocatalytic reactor as described in the first aspect for air or gas purification in a heating, ventilation and/or air conditioning system.

In yet another aspect, the present invention furthermore relates to a method of updating a heating, ventilation and/or air conditioning system, the method comprising replacing a section of the heating, ventilation and/or air conditioning system by a photocatalytic reactor as described in the first aspect. As the photocatalytic reactor can be made such that it fits a section of the HVAC system, replacement can be easy.

Further by way of illustration, embodiments of the present invention not being limited thereto, some further experiments were performed for illustrating the effectiveness of the systems according to embodiments of the present invention.

By way of illustration, two tests were performed, a first one at low concentrations of VOCs, corresponding with realistic VOC concentrations in the range 60 to 120 ppb. Furthermore, formaldehyde was also introduced in the system. A second test was performed at high concentrations of VOCs. In the latter case a concentration of about 1.5 ppm was introduced for four different types of VOCs. In this case no formaldehyde was introduced.

Figure 16:
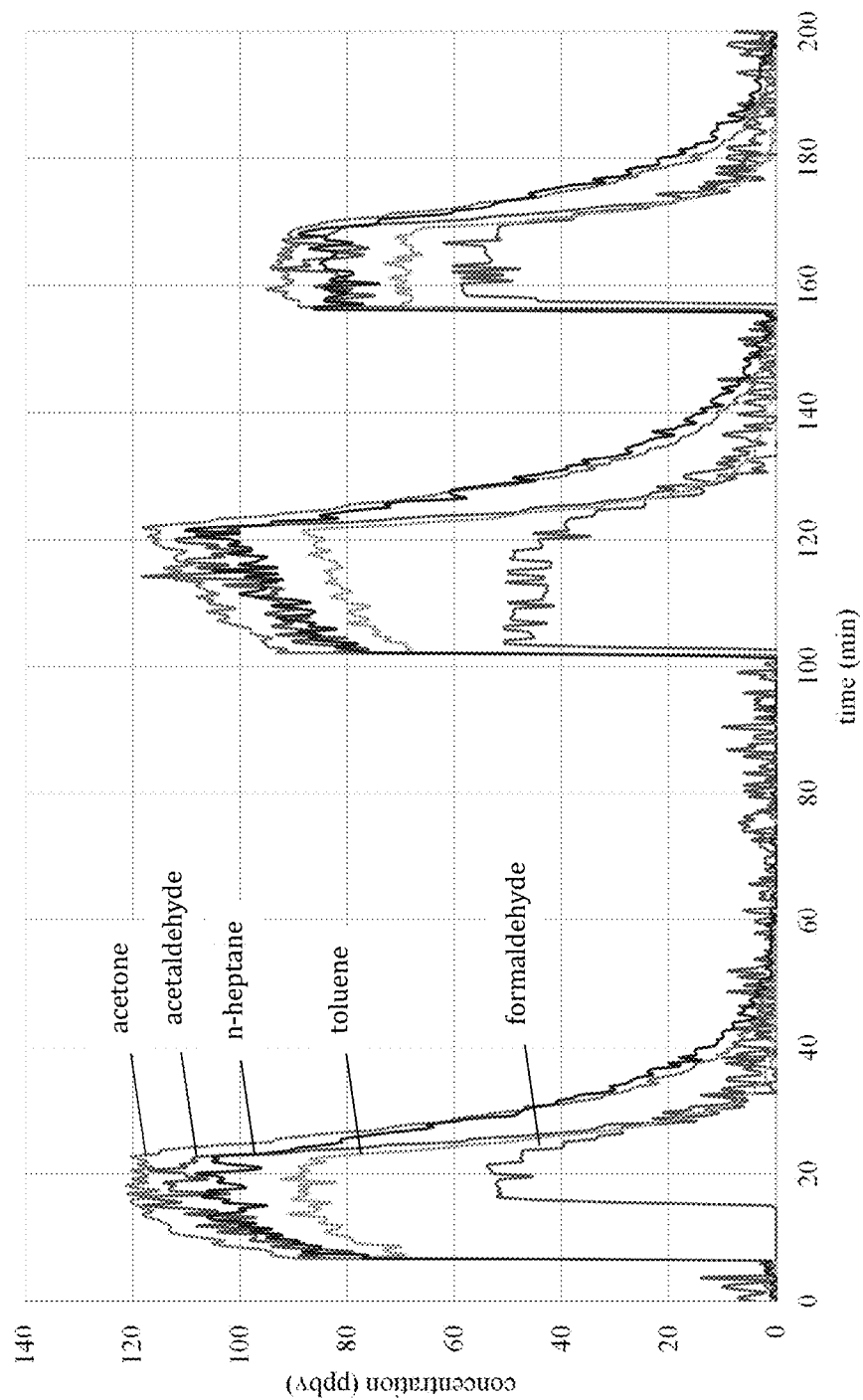
FIGS. 16 to 18 illustrates test results for a photocatalytic reactor according to an embodiment of the present invention for low and high VOC concentrations.

From the first experiment it can be seen that the reactor is breaking down the VOC concentrations provided accurately. The results are shown in FIG. 16. The graph in FIG. 16 illustrates the evolution of the VOC concentration versus time at low concentration. Except formaldehyde, the VOC mixture in liquid form (acetaldehyde, acetone, n-heptane and toluene) was introduced via a syringe. The clean air delivery rates (CADR) were calculated from these curves and are presented in table 4.

TABLE 4

| | CADR ($m^3/h$) | | | | |
|---|---|---|---|---|---|
| | Formaldehyde | Acetaldehyde | Acetone | Toluene | n-Heptane sum |
| Run 1 | 8 | 17 | 7 | 15 | 7 10 |
| Run 2 | 8 | 16 | 6 | 17 | 7 10 |
| Run 3 | 8 | 19 | 8 | 19 | 8 12 |

Figure 17:
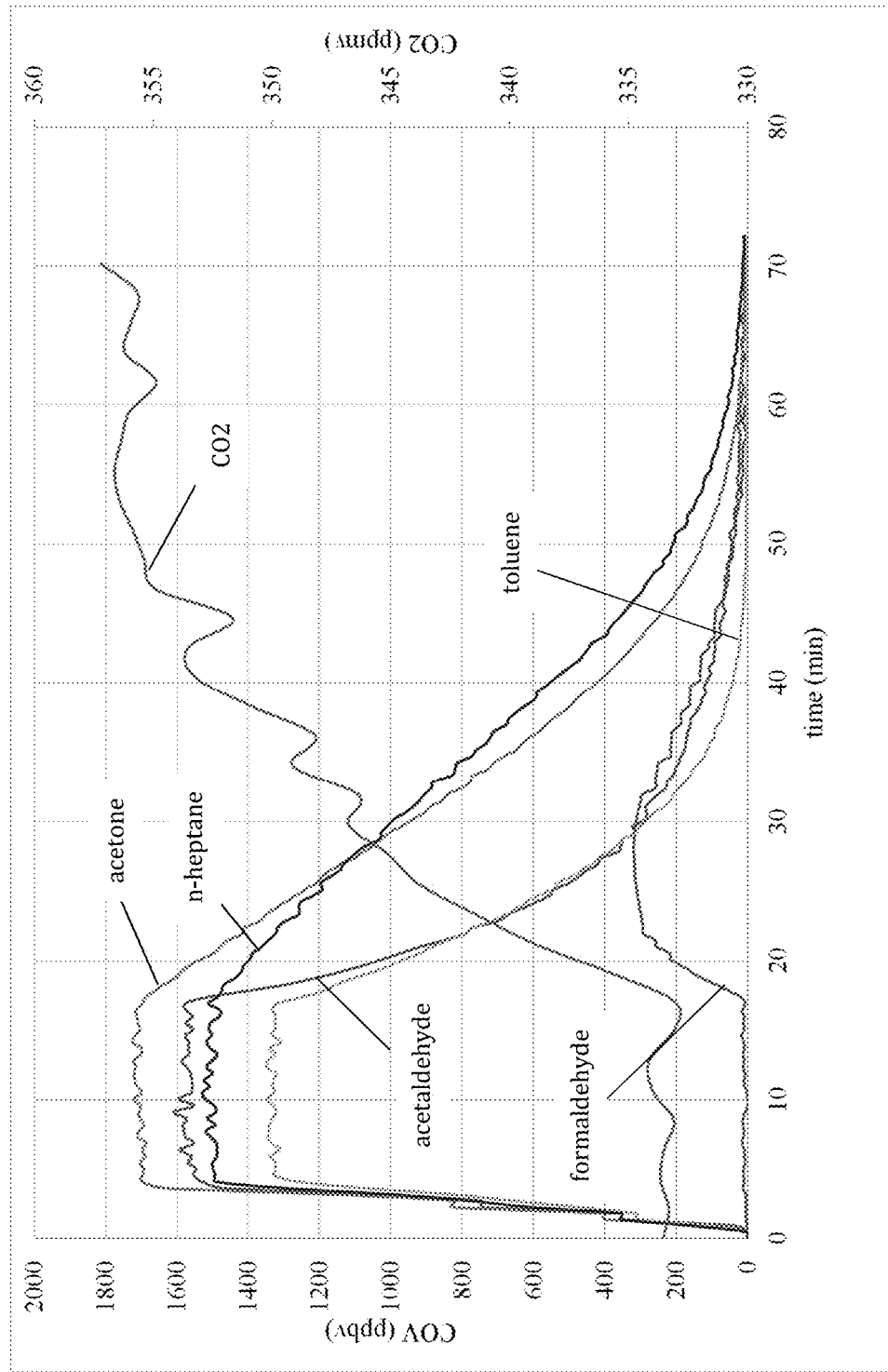
Figure 18:
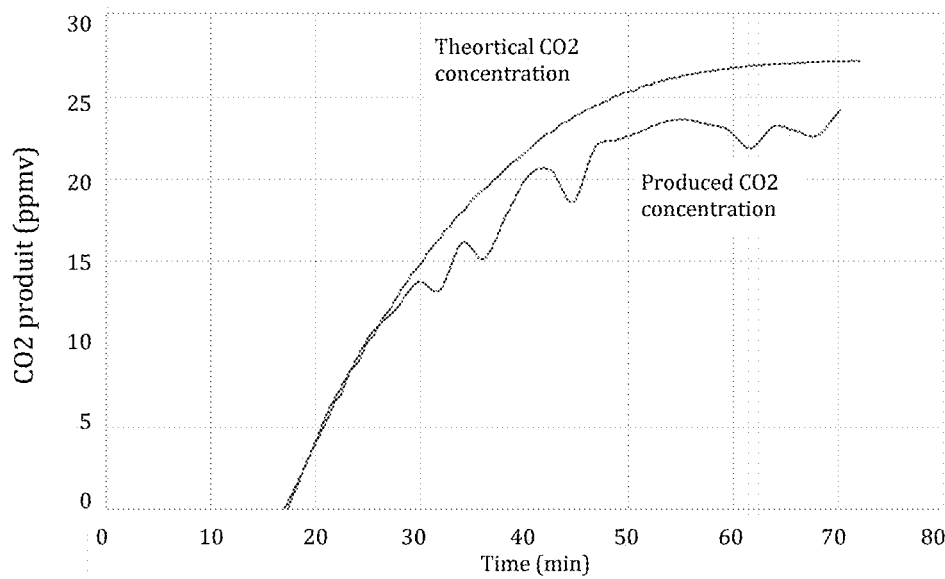

In the second experiment, whereby high concentrations of VOC were introduced, typically substantially higher than in normal operating conditions of HVAC systems. In the test, the mineralization process was studied at higher concentration with the VOC mixture of acetaldehyde, acetone, n-heptane and toluene around 1.5 ppm. Formaldehyde was not added. $CO_2$ evolution was followed. It can be concluded that the VOC and $CO_2$ concentration evolution versus time, as shown in FIG. 17 and the comparison of the theoretical $CO_2$ value and the actual produced $CO_2$ value as shown in FIG. 18, both indicate that good results are obtained with the photocatalytic reactor. The latter illustrates that there is a good mineralization from VOCs to $CO_2$. It can be seen that VOCs are breaking down fast. It was noted that at the moment the photocatalytic action starts by turning on the radiation sources, formaldehyde is formed. It is noted that it gets broken down quickly.

Figure 19:
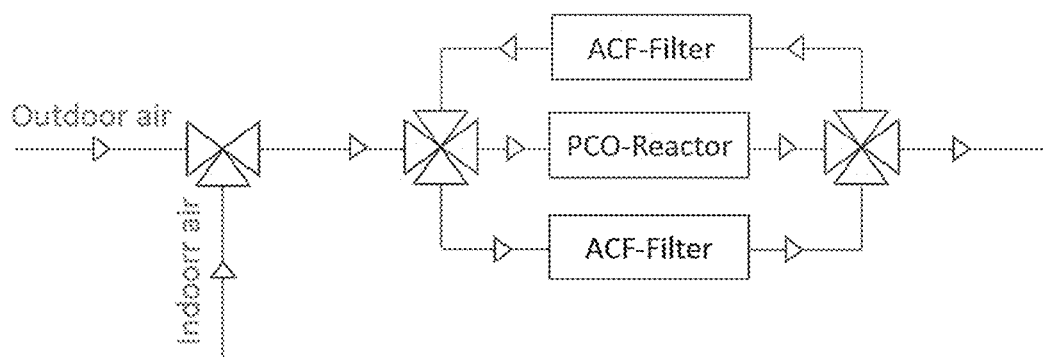
FIG. 19 illustrates a possible setup of a larger system including a photocatalytic reactor according to an embodiment of the present invention.

Nevertheless, in order to make sure that also formaldehyde or other pollutants are properly removed, a filter system according to embodiments of the present invention could also benefit from a setup combining active carbon adsorption with photocatalytic reactor treatment. A schematic representation thereof is shown in FIG. 19. In such a setup, the flow is sent alternatingly through different adsorbing filters for adsorbing VOCs and possible other pollutants. Once a filter is saturated, the filter can be connected with the photocatalytic reactor and cleaning of pollutants can be performed by releasing the pollutants from the active carbon filter and by allowing the photocatalytic reactor to perform its operation. By providing sufficient active carbon filters and photocatalytic reactor capacity, a continuous flow can be adequately handled. In this way, the present invention also relates to a photocatalytic reactor system comprising a photocatalytic reactor as described above, wherein the photocatalytic reactor system furthermore comprises one or more filters for first adsorbing VOC's and optional additional pollutants from a flow and for thereafter, when one of the filters is saturated, releasing the VOC's and the optional additional pollutants, the photocatalytic reactor system furthermore being adapted for treating the released VOC's and optional additional pollutants using the photocatalytic reactor.

The invention claimed is:

1. A photocatalytic reactor for use in a heating, ventilation and/or air conditioning system, the photocatalytic reactor comprising:
    a longitudinal housing, the longitudinal housing having a wall and comprising an inlet and an outlet for allowing air or gas to pass through along the longitudinal direction of the longitudinal housing,
    a plurality of tubes positioned in the longitudinal housing and arranged such that some outer tubes are positioned closer to the housing wall than some inner tubes, said plurality of tubes having their longitudinal axis parallel with the longitudinal axis of the longitudinal housing allowing said air or gas to pass along and through said tubes, said tubes furthermore comprising photocatalytic material in or on their tube walls, and
    an irradiation system for irradiating the photocatalytic material for inducing catalytic action,
    wherein the irradiation system and plurality of tubes are configured so that upon irradiating by the irradiation system the photocatalytic material of said outer tubes as well as of said inner tubes is irradiated,
    wherein the photocatalytic material comprises a calcinated material, said calcinated material including photocatalytic material having been heated after application of the photocatalytic material to the tubes as a powder-modified sol-gel with a photocatalytic powder concentration of up to 50 g/L, to a temperature of at least 400° C., and
    wherein the tubes are glass tubes.

2. The photocatalytic reactor according to claim 1, wherein the tubes are made of sodium free glass.

3. The photocatalytic reactor according to claim 1, wherein the cross-section of the tubes is any of circular, elliptical or polygonal.

4. The photocatalytic reactor according to claim 1, wherein the tubes are geometrically arranged such that the outer walls of the tubes form feedthroughs for air or gas to pass.

5. The photocatalytic reactor according to claim 4, wherein a cross-sectional area of each feedthrough is between 0.5 and 1.5 times an average cross-sectional area of the tubes.

6. The photocatalytic reactor according to claim 1, wherein the photocatalytic material is applied as coating on the inner and/or outer side of the tubes.

7. The photocatalytic reactor according to claim 1, wherein the number of tubes in the longitudinal housing is four or more.

8. The photocatalytic reactor according to claim 1, wherein the tubes are made of a material that is at least partly transparent for irradiation of said irradiation system, and/or
    wherein the tubes are stacked in a closed stacking configuration.

9. The photocatalytic reactor according to claim 1, wherein the photocatalytic material is positioned at an inner wall of the tubes, at an outer wall of the tubes or both at an inner wall and an outer wall of the tubes.

10. The photocatalytic reactor according to claim 1, wherein the walls of the housing are transparent or semitransparent for radiation of the irradiation system and wherein the irradiation system comprises one or more UV sources positioned outside the longitudinal housing.

11. The photocatalytic reactor according to claim 1, wherein the irradiation system comprises longitudinal irradiation sources positioned in the housing in between at least some outer tubes and at least some inner tubes.

12. The photocatalytic reactor according to claim 11, wherein the longitudinal irradiation sources comprise optical fibers in between at least some outer tubes and at least some inner tubes, said optical fibers being arranged for guiding irradiation from an irradiation source coupleable thereto.

13. The photocatalytic reactor according to claim 1, wherein the photocatalytic material comprises $TiO_2$, $ZnO$, $Cu_xO$, $Fe_2O_3$, $CdS$, $GaP$, $ZnS$ or $WO_3$.

14. The photocatalytic reactor according to claim 1, wherein the longitudinal housing has a cross-section substantially corresponding with a cross-section of a conventional section of a heating, ventilation and/or conditioning system.

15. The photocatalytic reactor system comprising a photocatalytic reactor according to claim 1, wherein the photocatalytic reactor system furthermore comprises one or more filters for first adsorbing VOC's and optional additional pollutants from a flow and for thereafter, when one of the one or more filters is saturated, releasing the VOC's and the optional additional pollutants, the photocatalytic reactor system furthermore being adapted for treating the VOC's and optional additional pollutants using the photocatalytic reactor.

16. The heating, ventilation and/or air conditioning system comprising the photocatalytic reactor according to claim 1.

17. The heating, ventilation and/or air conditioning system according to claim 16, wherein the transport of air or gas in the photocatalytic reactor is solely based on a fan or pumping unit of the heating, ventilation and/or air conditioning system and/or
wherein the system furthermore comprises a sensor for sensing a quality of air or gas in the system, and
wherein the system furthermore is adapted for activating the photocatalytic reactor as function of a sensed quality of air or gas in the system.

18. The method of updating the heating, ventilation and/or air conditioning system, the method comprising replacing a section of the heating, ventilation and/or air conditioning system by the photocatalytic reactor according to claim 1.

19. The photocatalytic reactor according to claim 1, wherein the photocatalytic powder comprises P25 $TiO_2$.

20. The photocatalytic reactor according to claim 1, wherein the calcinated material includes photocatalytic material having been heated after dip-coating application of the photocatalytic material as a P25 $TiO_2$ powder-modified sol-gel with a photocatalytic P25 $TiO_2$ powder concentration up to 50 g/L to borosilicate glass tubes, to a temperature of at least 500° C.

* * * * *